United States Patent
Brady et al.

[19]

[11] Patent Number: 6,142,999
[45] Date of Patent: *Nov. 7, 2000

[54] FOLDING DEVICE AND METHOD FOR AN INTRAOCULAR LENS

[75] Inventors: Daniel G. Brady, San Juan Capistrano; Michael Collinson, Goleta; Claude A. Vidal, Santa Barbara, all of Calif.

[73] Assignee: Allergan, Irvine, Calif.

[ * ] Notice: This patent is subject to a terminal disclaimer.

[21] Appl. No.: 09/316,606

[22] Filed: May 21, 1999

Related U.S. Application Data

[62] Division of application No. 08/987,864, Dec. 9, 1997, Pat. No. 5,947,974.

[51] Int. Cl.$^7$ ...................................................... A61F 9/00
[52] U.S. Cl. ................................................. 606/106; 606/1
[58] Field of Search ................................. 606/1, 107, 166

[56] References Cited

U.S. PATENT DOCUMENTS

| | | |
|---|---|---|
| 4,681,102 | 7/1987 | Bartell . |
| 4,862,885 | 9/1989 | Cumming . |
| 5,171,241 | 12/1992 | Buboltz et al. . |
| 5,176,686 | 1/1993 | Poley . |
| 5,190,552 | 3/1993 | Kelman . |
| 5,304,182 | 4/1994 | Rheinish et al. . |
| 5,643,276 | 7/1997 | Zaleski . |

FOREIGN PATENT DOCUMENTS 0402138   12/1990   European Pat. Off. .

*Primary Examiner*—Michael Buiz
*Assistant Examiner*—William W. Lewis
*Attorney, Agent, or Firm*—Stout, Uxa, Buyan & Mullins, LLP; Frank J. Uxa

[57] ABSTRACT

A folding device for holding and folding an IOL and adapted to allow a surgeon to select between loading the IOL into a removably attached IOL injector and between holding the IOL in a folded state for removal with a separate instrument. The folding device includes a pair of opposing sides, each having an upper surface. A plurality of retaining brackets extend upwardly from the upper surfaces of each side. The brackets are adapted for receiving and removably retaining the IOL injector. A hinge couples the sides together along a fold axis and allows the sides to retain the IOL therebetween. The hinge allows the sides to fold together from a planer position about a first fold direction when using the separate instrument and towards each other about a second fold direction when using the IOL injector. This allows the surgeon to select between attaching the IOL injector to the retaining brackets such that when the sides are folded about the second fold direction, the IOL is released from the sides and loaded into the load chamber and between folding the sides about the first fold direction such that the IOL is folded and maintained in a folded state.

15 Claims, 4 Drawing Sheets

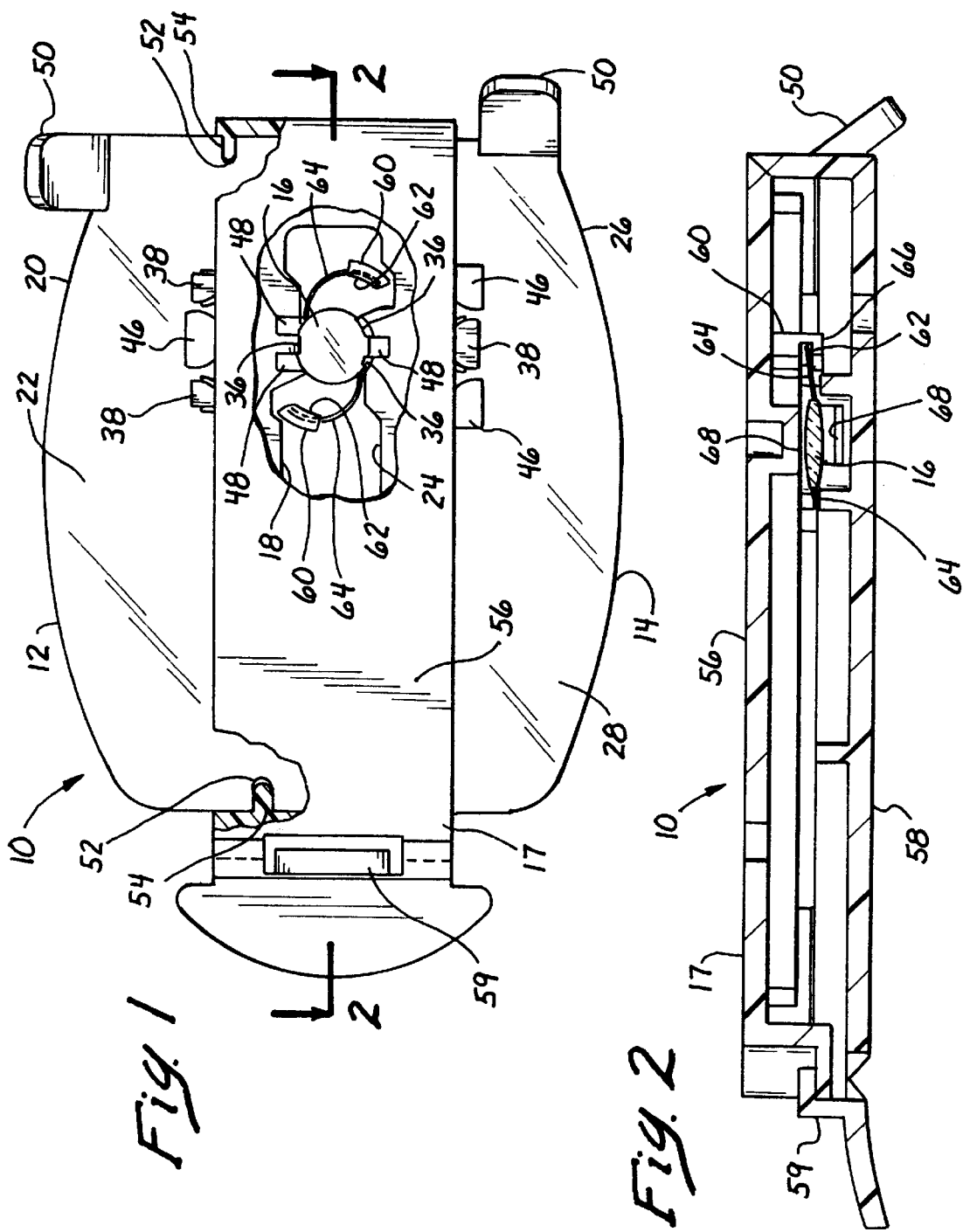

FOLDING DEVICE AND METHOD FOR AN
INTRAOCULAR LENS

This application is a division of application Ser. No. 08/987,864 filed Dec. 9, 1997, now U.S. Pat. No. 5,947,974.

FIELD OF THE INVENTION

This invention relates generally to intraocular lenses and, more particularly, to a folding device for holding and folding an intraocular lens in preparation for implantation into a patient.

BACKGROUND OF THE INVENTION

As is well known, an intraocular lens or IOL is used to replace the natural lens of the human eye when the natural lens becomes damaged or otherwise incapable of functioning. The natural lens is removed and the IOL is inserted into the eye as a direct replacement. A typical IOL includes an optic lens and one or more fixation members or haptics for fixing the IOL in the desired position within the eye.

The IOL is implanted directly into the eye through a small incision formed in the ocular tissue of the eye, outside the normal range of sight. To fit through this small incision, modern IOLs are designed to be deformed, e.g., folded, rolled or the like, to a relatively small profile and then allowed to naturally return to an initial nondeformed shape within the eye.

Insertion of the IOL through this small incision may be accomplished through use of a surgical instrument such as a pair of insertion forceps. In this technique, the IOL is first folded together to reduce its size. The folded IOL is then inserted into the incision and placed within the eye where it can unfold.

The IOL is typically provided to the surgeon or other medical personnel, in a packaging device which securely contains the IOL. These packaging devices protect the IOL during handling and transportation to the surgery facility and may even allow for accurately folding the IOL along the optic diameter in order to reduce its size. Because of their combined functions, these packaging devices are commonly termed holding and folding devices or folding devices. Some of these devices specifically fold the IOL in preparation for grasping by the forceps or other surgical instrument. An improved form of such a holding and folding device is described in Buboltz et al., U.S. Pat. No. 5,171,241.

A second technique for inserting an IOL into the eye includes the use of an IOL injector or cartridge, such as the IOL injector described in Bartell, U.S. Pat. No. 4,681,102. These IOL injectors include a load chamber which is connected to an injection tube. The load chamber includes an openable first lumen for receiving the IOL. Closure of this first lumen folds the IOL and maintains the IOL in a folded state. The injection tube includes a small diameter distal tip which is insertable into the incision within the eye. The IOL is transferable from the load chamber through the injection tube and into the eye. These IOL injectors simplify the placement of the IOL within the eye and reduce chances of surgeon error.

The IOL is provided to the surgeon in packaging. The IOL is removed from the packaging and placed on the open load chamber. The IOL is placed on the load chamber so that the IOL will be folded when the load chamber is closed.

The technique of removing the IOL from the packaging and transferring it to the load chamber is usually accomplished with a pair of forceps. Any covering of the packaging is removed such that the IOL is exposed. The forceps are used to physically remove the IOL and place it on the load chamber. This step requires steady hand operation of the forceps or similar device. The IOL can be dropped or may be damaged during this operation. There is thus, a need for a packaging system which simplifies the transfer of the IOL to the IOL injector.

During preparation for IOL insertion surgery, the surgeon may not know whether he or she will actually use insertion forceps, the IOL injector or another technique for insertion of the IOL. The procedure ultimately used may require that the IOL be supplied in a different packaging or require additional procedural steps such as pre-folding. It would be advantageous to provide a packaging system which is compatible with both the insertion forceps technique and the use of an IOL injector.

Accordingly, there is a need for a packaging device which can securely hold and protect an IOL during handling and transportation. There is also a need for a packaging device and method that can accurately fold an IOL in preparation for grasping by insertion forceps or alternatively can be used to directly load an IOL into the load chamber of an IOL injector. There is also a need for such a packaging device and method which is simple to use and inexpensive to manufacture.

SUMMARY

The present invention addresses the aforementioned needs by providing an IOL packaging or folding device which securely packages an IOL and can be used to fold the IOL for grasping with insertion forceps or alternatively can be coupled with an IOL injector for direct loading of the IOL. By providing a separate cover which surrounds the folding device, the IOL is securely contained and protected during handling and transportation.

More particularly, the present invention satisfies the need for a folding device which can be used to directly load the contained IOL into the load chamber of an IOL injector. By providing a pair of spaced apart and foldable sides which can be directly coupled with the wing flanges of the IOL injector, the folding device of the present invention can directly load the IOL into the load chamber. This direct loading eliminates the additional step of removing the IOL from the packaging device prior to placing it on the IOL injector.

In another aspect of the present invention, the folding device is adapted to allow a surgeon, or other medical personnel, to select between directly loading the contained IOL into the IOL injector as described above and, alternately, folding the IOL and holding the IOL in a folded state for removal by a separate surgical instrument. By providing the folding device having spaced apart planer sides which are hingably coupled about a fold axis and which retain the IOL in a grooved portion therebetween, the folding device of the present invention may be folded in a first direction for use with insertion forceps or other similar devices.

Alternatively, an IOL injector may be coupled to the folding device as described above. When coupled with an IOL injector, the folding device may be folded in a second direction, generally opposite to the first direction, such that the IOL is directly loaded into the load chamber. Grasping fingers are provided adjacent the load chamber to facilitate the transfer of the IOL from the folding device and into the IOL injector.

The present invention is generally directed to an IOL folding device adapted to be removably coupled with an IOL injector having a central load chamber and a pair of attached wings. The folding device comprises a first side having a first planer upper surface extending between a first inner edge and a first outer edge. The first inner edge is configured with a first internal groove. A second side having a second planer upper surface which extends between a second inner edge and a second outer edge is generally opposed to the first side. The second inner edge is also configured with a second internal groove. The first and second internal grooves are generally opposing and are dimensioned for receiving and retaining an edge of the IOL.

A hinge pivotally couples a portion of the first inner edge and the second inner edge along a fold axis. The hinge is adapted to allow the first and second sides to fold towards each other from a planer position in a first fold direction and also in a second fold direction, which preferably is generally opposite the first fold direction.

A plurality of retaining or attachment brackets extend upwardly from the first and second planer upper surfaces. The retaining brackets on each side are adapted to receive and removably retain one wing on the IOL injector. The retaining brackets are further configured to maintain each wing generally flat against the respective planer upper surface.

A pair of spaced apart constraints preferably protrude upwardly from the first planer upper surface. The constraints have a ramped surface which is oriented to direct one of the planer wings of the IOL injector into at least one of the retaining brackets on the first planer upper surface.

In another aspect of the present invention, the folding device is further configured to allow a surgeon or other user, to select between directly loading an IOL injector as described above and, alternately, folding the sides together in the first fold direction to fold the IOL and maintain the IOL in a folded state. Once in the folded state, the IOL can be grasped by a pair of insertion forceps of other surgical instrument.

In this aspect of the present invention, the folding device preferably further comprises a plurality of openings which extend through the respective side. Each of the openings is positioned on the planer upper surface and sized to receive at least one of the plurality of retaining brackets and the constraint on the opposing side. This allows the sides to be folded together from the planer position in which the sides are aligned and parallel and a folded position in which the side are flat against each other. The folded position maintains the IOL in a folded state and in its minimized size.

In yet another aspect of the present invention, the folding device includes a cover for protecting the IOL. The cover includes a top and bottom portion which surround the folding device and prevent the ingress of potential contaminants. An IOL seating portion as well as haptic constraints maintain the IOL in a desired configuration while maintained in the folding device.

In a further aspect of the present invention, the IOL injector is specifically configured for improved operation with an IOL and the present folding device. The IOL injector comprises a load chamber having a first, preferably semi-cylindrical, portion coupled to a second, preferably semi-cylindrical portion, along a first longitudinal edge to form a hinge. The portions are movable about the hinge between an open position and a closed position. The load chamber is configured to receive the IOL in the open position and to fold said IOL when moved to said closed position.

A planer wing or flange is attached to each of the first and second portions for moving the load chamber between the open and closed positions. Specifically, each of the planer wings is coupled to a second longitudinal edge on each of the first and second portions. The planer wings are configured to lie flat against each other when the load chamber is in the closed position.

Preferably, a grasping finger protrudes from each of the opposing planer wing surfaces and includes a beveled or otherwise sharpened tips for engaging an edge of the IOL and for retaining the IOL within the load chamber. A small slot or opening preferably is provided on each wing opposite each grasping finger. The slots are each configured to receive the opposing grasping finger such that the wings may be fully folded together.

An injection tube is joined to the load chamber and is adapted to receive the folded IOL from the first lumen. The injection tube includes an open distal end in communication with the load chamber and through which the folded IOL passes to be inserted into the eye.

A method, according to the principles of the present invention, for holding an IOL in preparation for insertion into an eye of a patient, includes the steps of providing a foldable IOL and a folding device for retaining and folding the IOL. The folding device, such as the folding device of the present invention, is adapted and configured to allow a surgeon to select between loading an IOL injector with the IOL and, alternately, folding the IOL into a folded position for removal with a separate instrument. The folding device is foldable in a first fold direction to fold the IOL in one direction and in a second fold direction, preferably opposite the first fold direction, for loading into the IOL injector.

The IOL is inserted into a pair of generally opposing internal grooves within the folding device. This step of inserting includes placing an edge of the IOL into an internal groove within an inner edge on each of the sides of the folding device.

If the surgeon decides to utilize an IOL injector for insertion of the IOL, the IOL injector must be provided and removably attached to the folding device. The provided IOL injector includes a load chamber having a pair of opposing, preferably semi-cylindrical, portions which are pivotally coupled along a first longitudinal edge as previously described. The IOL injector also includes a pair of planer wings. Each wing is attached along a second longitudinal edge of each semi-cylindrical portion. The IOL injector is attached to the folding device such that the planer wings are generally retained flat against each of the planer upper surfaces.

After the IOL injector is attached, the folding device and the IOL injector are together folded in a fold axis and in a second fold direction. This folding step allows the IOL to be removed from the folding device and moved into the load chamber of the IOL injector. The IOL injector, now containing the IOL, is removed from the folding device and the wings of the IOL injector are closed such that the IOL is folded within the load chamber.

In another aspect of the present invention, the surgeon may decide to use a surgical instrument, such as a pair of insertion forceps, to remove the IOL from the folding device. In this aspect, the IOL injector is not necessary and is not attached to the folding device. The folding device, containing the IOL, is folded about the fold axis in a first direction. The surgical instrument is then used to remove the folded IOL.

The invention, together with additional features and advantages thereof, may be best understood by reference to the following description taken in conjunction with the accompanying illustrative drawings.

BRIEF DESCRIPTION OF THE DRAWINGS

FIG. 1 is a top view of an embodiment of a folding device having the features of the present invention and showing a cut-away portion to expose a contained IOL;

FIG. 2 is a sectional view of the folding device taken along lines 2—2 of FIG. 1;

DESCRIPTION OF THE PREFERRED EMBODIMENTS

Figure 3:
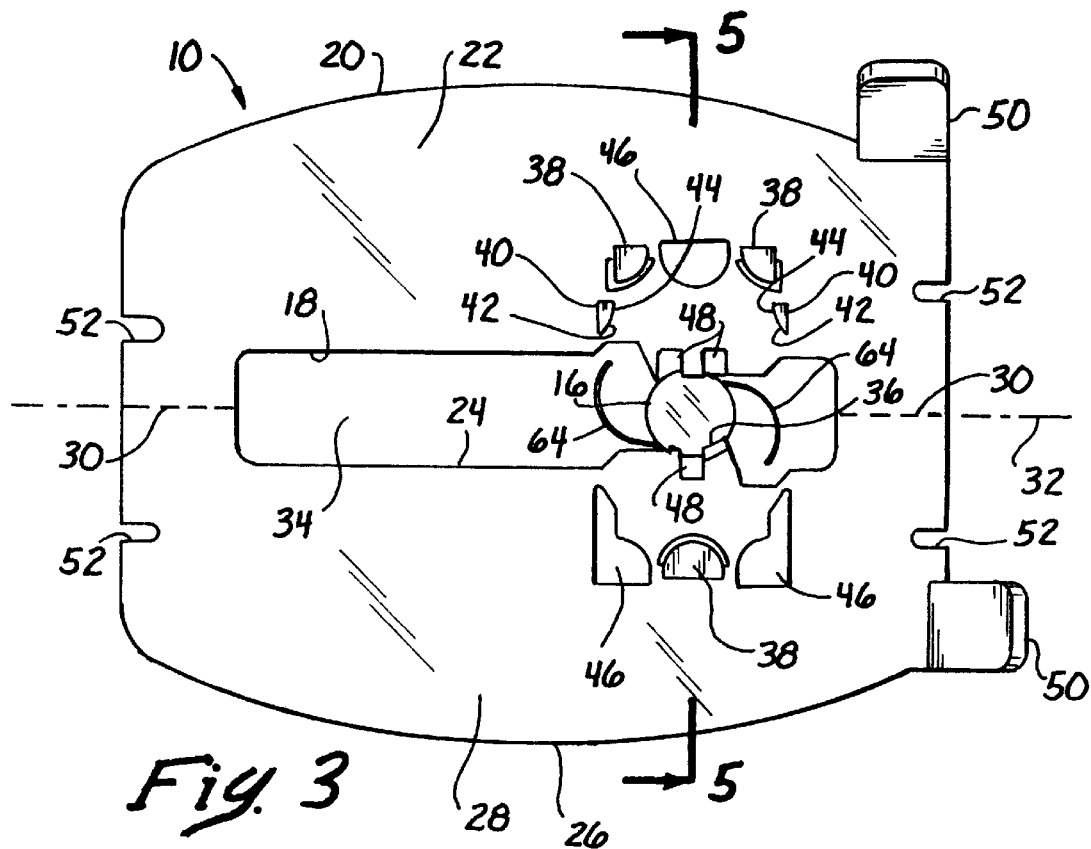
FIG. 3 is a top view of the folding device shown in FIG. 1, shown with the cover removed.

Referring now to the drawings, wherein like reference numerals designate identical or corresponding parts throughout the several views and embodiments, a folding device according to the principles of the present invention is illustrated in FIGS. 1 and 2, and designated by reference numeral 10. As shown, the folding device 10 generally includes a first side 12 and a second side 14 which are configured to hold a foldable IOL 16 therebetween. A removable cover 17 may be provided which is placed around the sides 12 and 14 to further secure the IOL 16 and to protect from ingress of contaminants.

Figure 4:
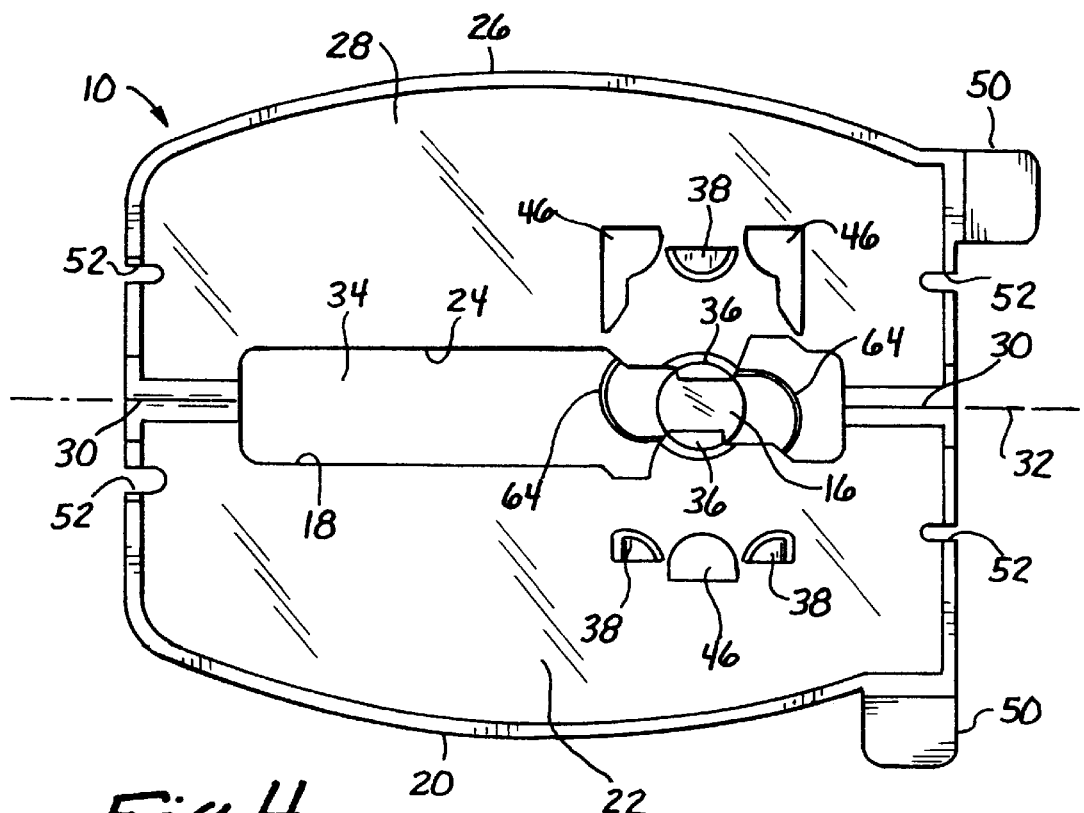
FIG. 4 is a bottom view of the folding device shown in FIG. 1, shown with the cover removed.
Figure 5:
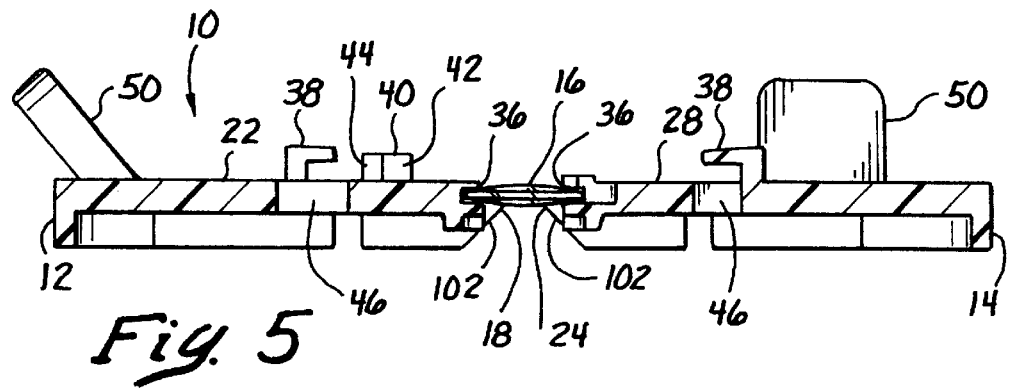
FIG. 5 is a sectional view of the folding device taken along lines 5—5 of FIG. 3.

Referring now, to FIGS. 3 through 5, the folding device 10 will be described in greater detail. In particular, The first side 12 extends between a first inner edge 18 and a first outer edge 20 and includes a first upper surface 22. In a similar configuration, the second side 14 extends between a second inner edge 24 and a second outer edge 26 and includes a second upper surface 28. Preferably, each of the upper surfaces 22 and 28, is generally planer or flat. However, other configurations may be used and particularly, an over biting lip or similar structure, may be provided around the outer edges 20 and 26 of the sides 12 and 14. The lip may further protect the IOL and prevent the ingress of contaminants.

A hinge 30 pivotally couples the first and second sides 12 and 14 about their inner edges 18 and 24 and about a fold axis 32. Preferably, the hinge 30 includes a pair of spaced apart hinge portions aligned along the fold axis 32 with a slot 34 therebetween, and is best illustrated in FIGS. 3 and 4. The slot 34 also provides a spacing between a portion of the inner edges 18 and 24. The hinge 30 allows the sides 12 and 14 to fold towards each other from a planer position, as also illustrated in FIGS. 3 and 4.

Each of the first inner edge 18 and the second inner edge 24, may include a specifically configured region 36 for retaining the IOL 16. Preferably, each of these configured regions 36 comprises an opposing internal groove or similar cutout for receiving a portion of the IOL 16. Each internal groove 36 may be sized and dimensioned to receive and retain an edge of the IOL 16 and is preferably aligned with the fold axis 32.

A retaining bracket 38 extends upwardly from each of the first and second upper surfaces 22 and 28. Preferably, the first upper surface 22 includes a pair of spaced apart retaining brackets 38 and the second upper surface 28 includes a single retaining bracket, generally opposing those on the first side 12. The retaining brackets 38 are configured for receiving and removably retaining an IOL injector against the folding device 10 as will be described in greater detail below.

At least one of the upper surfaces 22 and 28 may be fitted with an alignment member or constraint 40 for guiding a portion of the IOL injector into the retaining brackets 38. The constraint 40 may include a specially configured first surface 42, such as a ramped surface which is oriented to direct the portion of the IOL injector into the retaining brackets 38. The constraint 40 may also include a second surface 44 which maintains the IOL injector in position within the retaining brackets 38. Preferably, a pair of constraints 40 protrude upwardly from the first upper surface 22. The constraints 40 may be spaced apart and facing inwardly with the ramped surfaces 42 generally opposing.

The second side 12 may be configured with at least one opening 46 which extends through the second upper surface 28 and is configured for receiving the retaining brackets 38 and the constraints 40 on the first upper surface 28. In a similar fashion, the first side 12 may also include at least one opening 46 which extends through the first upper surface 22 and is configured for receiving any retaining brackets 38 and constraints 40 that protrude upwardly from the second upper surface 28.

Figure 8:
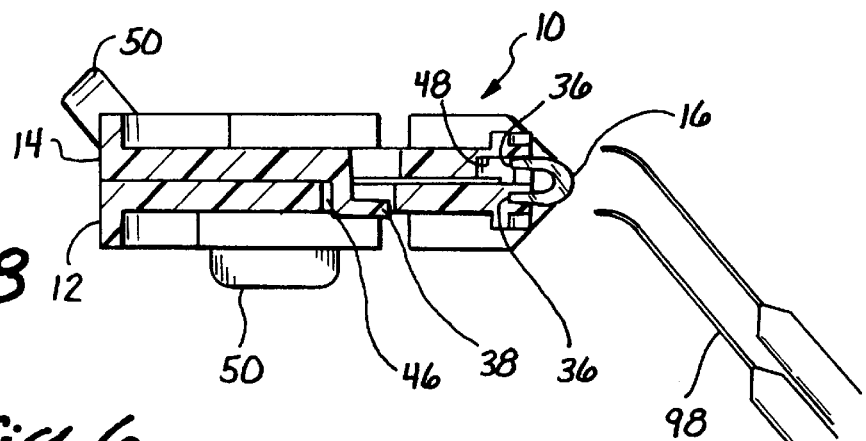
FIG. 8 is a side view of the folding device of FIG. 5, shown in the folded position.

The openings 46 allow the sides 12 and 14 to fold together about a first direction such that the first upper surface 22 and the second upper surface 28 lie flat against each other in a folded position as best illustrated in FIG. 8. This is accomplished because each of the retaining brackets 38 and the constraints 40 pass through an opening 48. Preferably, the first side 12 includes one hole or opening 46 for receiving the opposing retaining bracket 38 on the second upper surface 28 and the second side 14 includes a pair of spaced apart holes 46, each for receiving the opposing retaining bracket 38 and constraint 40 on the first upper surface 22.

At least one of the first and second upper surfaces 22 and 28 may be configured with a second slot or groove 48. This second groove 48 may be aligned generally transverse to the respective internal groove 36 and may terminate or commence at or into the internal groove 36. The groove 48 is configured and oriented for use with a removal device which can remove the IOL 16 from within the internal grooves 36. Preferably the removal device is a grasping finger on the IOL injector as will be described in greater detail below.

In a preferred configuration, the first upper surface 22 includes a pair of spaced apart second grooves 48. These grooves 48 are transverse to the respective internal groove 36 as well as generally perpendicular to the fold axis 32. In a similar fashion, the second upper surface 28 includes a single second groove 48 generally oriented opposing and between the spaced apart second grooves 48 on the first upper surface 22. This configuration is best illustrated in FIG. 3.

Handling tabs 50 may be provided on each of the sides 12 and 14. The handling tabs 50 may simplify handling of the sides 12 and 14. In particular, the handling tabs 50 simplify the opening of the sides 12 and 14 from the folded position.

Preferably, each of the sides 12 and 14 includes at least one handling tab 50.

Referring now, back to FIGS. 1 and 2, the cover 17 includes a top portion 56 and a bottom portion 58 which generally surround the sides 12 and 14. The cover 17 protects the IOL 16 and maintains the IOL in its original dimensions while it is maintained between the sides 12 and 14. In addition, the cover 17 may be configured to prevent contaminants and debris from reaching the IOL 16 while keeping the IOL from moving during shipping and handling. A latching device 59 secures the top and bottom portions 56 and 58 together.

A plurality of alignment notches 52 may be provided in each of the sides 12 and 14. The alignment notches 52 may be configured for operation with corresponding alignment tabs 54 on the cover 17. When mated, the alignment notches 52 and tabs 54 secures the sides 12 and 14 relative to the cover 17.

A pair of haptic constraining members 60 may extend from either of the top or bottom portions 56 and 58. Preferably, these members extend between the top and bottom portions 56 and 58 and are fitted with slot or groove 62 for retaining a haptic 64 on the IOL 16. More preferably, the haptic constraining members 60 comprise two generally opposing members which extend from the top portion 56. Each constraining member 60 may have a ramped or otherwise specially configured distal end 66 which allows the haptic 64 to more easily fall into the groove 62.

The cover 17 may also be fitted with upper and lower IOL supporting bases 68. Each of these bases 68 may be dimensioned to support the respective surface of the IOL 16 and to maintain the original or natural dimensions of the IOL. Preferably, one supporting base 68 extends downwardly from the top portion 56 and another supporting base 68 extends upwardly from the bottom portion 58. Each supporting base 68 is located either over or under the IOL 16.

Figure 6:
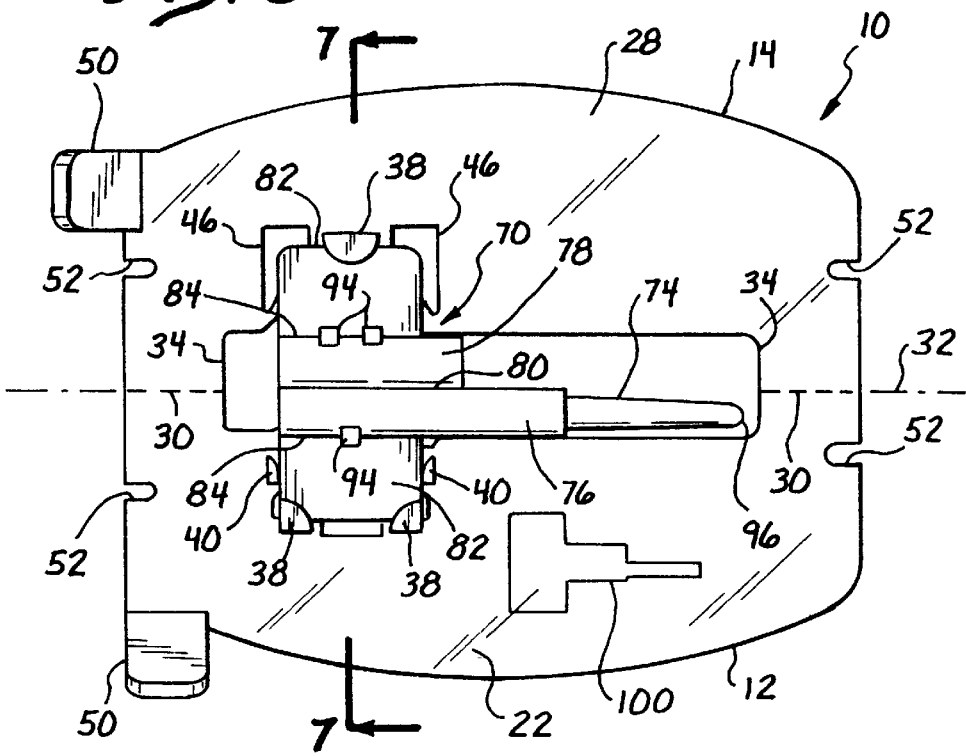
FIG. 6 is a top view of the folding device of FIG. 3 shown with an attached IOL injector.
Figure 7:
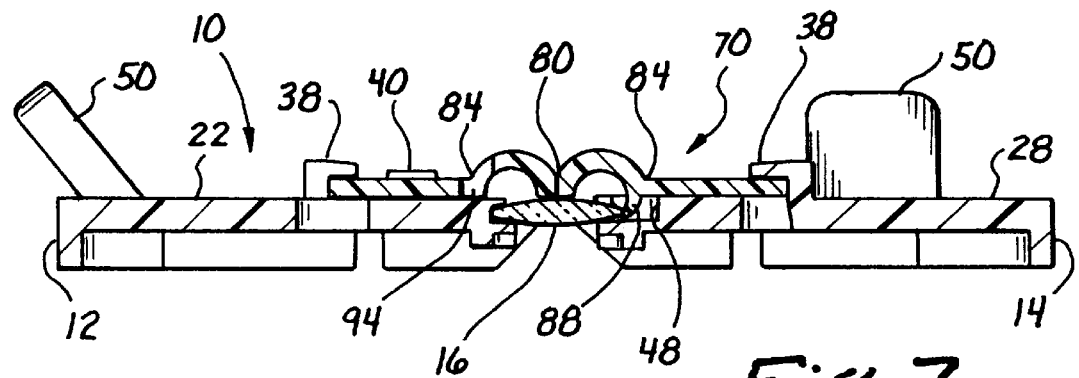
FIG. 7 is a sectional view of the folding device and attached IOL injector taken along lines 7—7 of FIG. 6.

As previously mentioned, and as best illustrated in FIGS. 6 and 7, the folding device 10 of the present invention may be removably coupled with an IOL injector 70. In general, the IOL injector 70 may be coupled to the sides 12 and 14 and against the upper surfaces 22 and 28 through the retaining brackets 38. The IOL injector 70 is used to insert the IOL 16 into an eye of a patient (not shown) as is well known.

Figure 10:
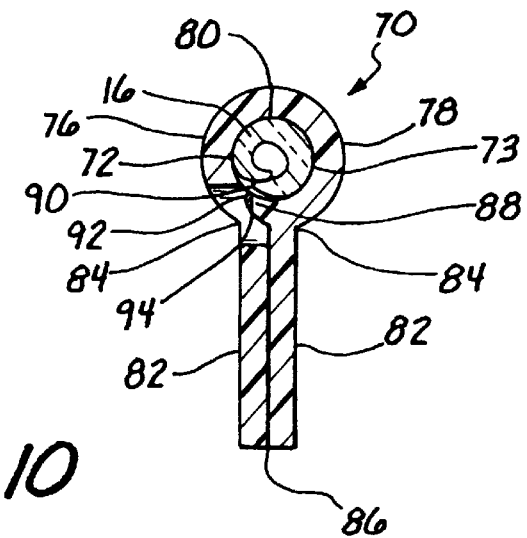
FIG. 10 is a side view of an IOL injector according to the principles of the present invention.

More particularly, the IOL injector 70 of the present invention includes a central load chamber 72 defining a first lumen 73 and an injection tube 74. The load chamber 72 has a first semi-cylindrical portion 76 coupled to a second semi-cylindrical portion 78 along a first longitudinal edge 80 to form a hinge. Each of the semi-cylindrical portions 76 and 78 are movable about the hinge between an open position, as best illustrated in FIG. 6, and a closed position which defines the first lumen 73, and is best illustrated in FIG. 10. The load chamber 72 is adapted to receive the IOL 16 when in the open position and to fold the IOL when moved to the closed position.

A flanged member or wing 82 is coupled to a second longitudinal edge 84 on each of the first and second semi-cylindrical portions 76 and 78. The generally opposing wings 82 are used to move and maintain the semi-cylindrical portions 76 and 78 between the open and closed positions. The wings 82 may be dimensioned such that each wing 82 fits into the retaining bracket 38 on the respective upper surfaces 22 and 28. Preferably, each of the wings 82 has an opposing planer surface 86 so that they lie flat against the upper surfaces 22 and 28 and may be fully moved together when in the closed position.

At least one grasping finger 88 may extend or protrude inwardly from at least one of the wings 82. Preferably, one of the wings 82 includes a first grasping finger 88 and the other wing includes a pair of opposing grasping fingers. The grasping fingers 88 may each have an inner surface 90 which forms a cylindrically shaped extension of the respective semi cylindrical portions 76 and 78 when the IOL injector 70 is coupled to the sides 12 and 14. Each of the grasping fingers 88 may also have a pointed or sharpened distal end 92 for movement within one of the second grooves 48 and for engaging an edge of the IOL 16. The grasping fingers 88 may also be useful in folding the IOL 16 and maintaining the IOL within the load chamber 72.

Each of the wings 82 may be configured with an opening or slot 94 opposite each of the grasping fingers 88 on the opposing wing. Each slot 94 is dimensioned and adapted to receive the opposing grasping finger 88 such that the wings 82 lie flat against each other when the IOL injector 70 is in the closed position. Preferably, one of the wings 82 includes a single grasping finger 88 between two adjacent slots 94 and the opposing wing includes two spaced apart grasping fingers straddling a single slot.

The injection tube 74 is joined to the load chamber 72 and configured to receive the folded IOL 16 from the load chamber. The injection tube 74 includes a central passageway and an open distal end 96. The open passageway and distal end 96 are connected and in open communication with the load chamber 72. The folded IOL 16 is moved from the first lumen 73 through the injection tube 74 and out the distal end 96 to be inserted into the eye.

Referring back now to FIGS. 1–10, a method of holding an IOL in preparation for insertion into an eye of a patient will be described. The method includes the steps of providing a foldable IOL 16 and a folding device, such as the folding device 10 of the present invention. The folding device 10 securely holds the IOL 16 and is adapted to allow a surgeon or other personnel to select between at least two insertion techniques. More particularly, the folding device 10 allows the surgeon to fold the IOL 16 and maintain the IOL in a folded state for removal by a separate instrument 98. The folding device 10 may also be coupled with a removable IOL injector, and preferably, the IOL injector 70 of the present invention, for direct loading of the IOL 16 into the load chamber 72. Thus, the folding device 10 of the present invention advantageously allows the surgeon to have at least two techniques for handling the IOL 16.

Preferably, the IOL 16 is inserted into the folding device 10 prior to reaching the surgeon and more preferably, prior to transportation or other handling. This step of insertion may include placing the IOL 10 between the sides 12 and 14 such that the edge of the IOL is retained within the opposing internal grooves 36. The sides 12 and 14 may be maintained in a planer position to simplify this insertion and to better secure the IOL 16, as best illustrated in FIG. 5.

A cover, such as the cover 17 may be used to further secure and protect the IOL. The cover 17 may be placed around the folding device 10 such that the top and bottom portions 56 and 58 surround a portion of each of the sides 12 and 14. The alignment tabs 54 may be fitted into the alignment notches 52 to secure the sides 12 and 14 and prevent their movement from the planer position. Sidewalls (not shown) may be provided around the top and bottom portions 56 and 58 of the cover 17 to further secure the sides 12 and 14 and to prevent contamination from reaching the IOL 16.

Preferably, the cover 17 is coupled to the folding device 10 prior to the insertion of the IOL 16. This allows the IOL 16 to be supported by both the internal grooves 36 within the folding device 10 and at least one of the supporting bases 68 on the cover 17. If the IOL 16 is configured with haptics 64, they may be fitted into the haptic constraining members 60. Particularly, each haptic 64 may be slid into the respective haptic groove 62. The haptic constraining members 60 secure the IOL 16 and protect the haptics 64.

The cover 17 may be closed around the folding device and the latching device 59 latched. This latching device 59 may be a one use latch, such that once the cover is opened, it cannot be resealed. The IOL 16 is now packaged and ready for handling and transportation to the surgeon or other personnel. Once the surgeon is ready to insert the IOL 16, the latching device 59 may be opened and the cover removed.

As mentioned, the folding device 10 of the present invention securely holds the IOL 16 and advantageously allows the surgeon to select between folding the IOL and maintaining the IOL in a folded state and between attaching the IOL injector 70 and loading the IOL into the load chamber 72. If the surgeon selects to fold the IOL 16 and hold the IOL in the folded state, the sides 12 and 14 may be folded together about the fold axis 32. This moving of the sides 12 and 14 folds the IOL 16 about the fold axis 32 while retaining the edges of the IOL within the internal grooves 36. Preferably, the sides 12 and 14 are folded about a first fold direction until they are flat against each other, as best illustrated in FIG. 8. The separate instrument 98 may then be used to grasp and remove the folded IOL 16 in preparation for insertion into the eye. The separate instrument 98 may be a pair of insertion forceps or other insertion device. Alternatively, the folded IOL 16 may be placed in a separate insertion device.

If the surgeon elects to utilize an IOL injector 70 for insertion of the IOL 16, the IOL injector may be removably coupled to the folding device 10. Alternatively, the folding device 10 may be supplied to the surgeon or other user with the IOL injector 70 attached. An indicator or marking 100 may be placed on at least one of the upper surfaces 22 and 28 to indicate the proper attachment orientation of the IOL injector 70. The indicator marker 100, which may be imprinted or otherwise formed within the side 12, reduces the chance of mistakes when attaching the IOL injector 70.

The IOL injector 70 is attached to upper surfaces 22 and 28 of the folding device 10 through the retaining brackets 38. More specifically, the IOL injector 70 is moved to the open position such that the wings 82 are apart. Each wing 82 may then be placed against the respective upper surface 22 and 28, such that the first lumen 73 faces downward and into the folding device 10. The wings 82 may then be slid into the retaining brackets 38. The wings 82 may also be slid against the constraints 40 to guide the wings 82 into the respective retaining bracket 38. The retaining brackets 38 maintain the wings 82 flat against the respective upper surface 22 and 28, as best illustrated in FIGS. 6 and 7. Preferably, the wings 82 are spread apart and slid into the retaining brackets 38 in a simple continuous motion.

Figure 9:
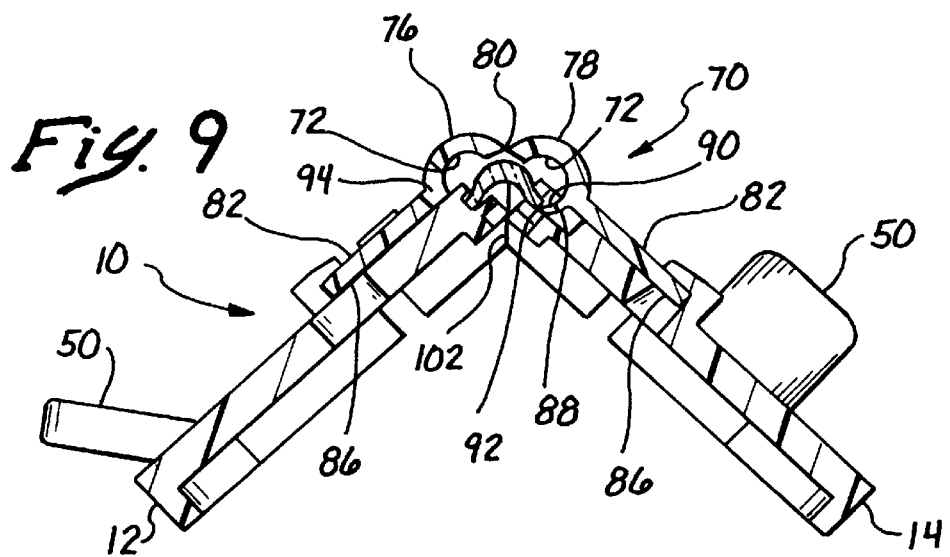
FIG. 9 is a sectional view of the folding device and attached IOL injector of FIG. 7, shown in a folded position.

Once the IOL injector 70 is attached, the folding device 10 with the inserted IOL 16 may be folded. This folding step comprises folding or otherwise moving the sides 12 and 14 together from the planer position about a second fold direction to a folded position. Preferably, the second fold direction is opposite the first fold direction. Thus, the folding device 10 is folded about the first fold direction for use with the separate instrument 98 and about the second fold direction when using the IOL injector 70. An installed IOL injector 70 prevents the folding device 10 from being folded about the first fold direction. Mechanical stops 102 may be used to define the folded position about the second fold direction, as illustrated in FIG. 9.

Once the folding device 10 and coupled IOL injector 70 are in the folded position, the IOL 16 may be loaded and the IOL injector removed. This step includes removing the IOL 16 from within the opposing internal grooves 36 of the folding device 10 and moving it into the load chamber 72. The IOL injector 70 may be removed from the folding device 10 by sliding the wings 82 out of the retaining brackets 38 and pulling the IOL injector away from the folding device. This action may simply require grasping the load chamber 72 while closing the wings 82.

As the wings 82 are closed and pulled out of the retaining brackets 38, the grasping fingers 88 slide through the second grooves 48 and into the internal grooves 36 to capture the IOL 16. Further removal of the IOL injector 70 from the folding device 10 removes the IOL 16 and loads the IOL into the load chamber 72. As the wings 82 are moved together to the closed position, the IOL 16 is folded within the first lumen 73 of the load chamber 72.

While this invention has been described with respect of various specific examples and embodiments, it is to be understood that various modifications may be made without departing from the scope thereof. For example, various sizes of the folding device are contemplated as well as various types of construction materials. Also, various modifications may be made to the configuration of the parts and their interaction. Therefore, the above description should not be construed as limiting the invention, but merely as an exemplification of preferred embodiments thereof and that the invention can be variously practiced within the scope of the following claims.

What is claimed is:

1. A folding device for holding an intraocular lens and for loading the intraocular lens into an intraocular lens injector having a load chamber, said folding device comprising:

an intraocular lens holding assembly including a first side and a second side together defining a slot for retaining the intraocular lens, the intraocular lens holding assembly being adapted to receive and removably retain an intraocular lens injector having a load chamber;

a hinge pivotally coupling said first side and said second side along a fold axis, said hinge adapted to allow the first and second sides to fold towards each other from a substantially planer position; and wherein the intraocular lens holding assembly is adapted to retain an intraocular lens injector having a load chamber such that when the first and second sides are folded together and the intraocular lens injector is removed the intraocular lens is removed from the slot and loaded into the load chamber of the intraocular lens injector.

2. The folding device of claim 1 wherein the first side comprises a first upper surface extending between a first inner edge and a first outer edge, and the second side comprises a second planer upper surface extending between a second inner edge and a second outer edge, each of the first and second inner edges having an internal groove generally aligned with the fold axis and dimensioned for receiving and retaining an edge of the intraocular lens.

3. The folding device of claim 2 which further comprises an indicator marker on one of the first and second upper surfaces for indicating the proper attachment orientation of an intraocular lens injector having a load chamber.

4. The folding device of claim 2 which further comprises a groove on the first upper surface, the groove being generally traverse to the internal groove of the first inner edge and terminating in the first internal groove, the groove being adapted to expose an edge of the intraocular lens.

5. The folding device of claim 1 which further comprises an intraocular lens injector having a load chamber removably attached to the intraocular lens holding assembly.

6. The folding device of claim 1 which further comprises a removable cover adapted to cover the intraocular lens holding assembly and to maintain the intraocular lens within the slot.

7. A folding device for holding and folding an intraocular lens, the folding device adapted to allow a surgeon to select between loading the intraocular lens into a removably attached intraocular lens injector and, alternately, removing the intraocular lens in a folded state with a separate instrument, the folding device comprising:

an intraocular lens holding assembly including a first side; and a second side;

a hinge coupling the first side and the second side along a fold axis and adapted to allow the sides to retain the intraocular lens and to fold together from a substantially planer position in a first fold direction when using the separate instrument and in a different second fold direction when using the intraocular lens injector; and the intraocular lens holding assembly being adapted to receive and removably retain the intraocular lens injector.

8. The folding device of claim 7 wherein the intraocular lens holding assembly further includes a plurality of retaining brackets positioned on the first and second sides and adapted to facilitate receiving and removably retaining the intraocular lens injector by the intraocular lens holding assembly.

9. The folding device of claim 7 wherein the first side includes a first inner edge defining a first internal groove and the second side includes a second inner edge defining a second internal groove generally opposing the first internal groove, each of the internal grooves dimensioned for receiving and retaining an edge of the intraocular lens.

10. The folding device of claim 7 which further comprises an intraocular lens injector having a load chamber removably attached to the intraocular lens holding assembly.

11. The folding device of claim 9 which further comprises a removable cover adapted to cover the intraocular lens holding assembly and to maintain the intraocular lens within the opposing internal grooves.

12. A method of holding an intraocular lens in preparation for insertion into an eye of a patient, the method comprising:

providing a intraocular lens holding assembly holding a foldable intraocular lens, the intraocular lens holding assembly having a first side pivotally coupled to a second side along a fold axis, the sides being foldable in a first fold direction and in a second fold direction different from the first fold direction.

13. The method of claim 12 which further comprises the step of placing a cover over the intraocular lens holding assembly.

14. The method of claim 12 which further comprises the steps of folding said intraocular lens holding assembly in said first fold direction, and, thereafter, using a separate instrument to remove the folded intraocular lens for said intraocular lens holding assembly.

15. The method of claim 12 which further comprises the steps of providing an intraocular lens injector removably attached to said intraocular lens holding assembly, folding said intraocular lens holding assembly in said second fold direction, and removing said intraocular lens and said intraocular lens injector together from said intraocular lens holding assembly.

* * * * *